(12) United States Patent
Chen et al.

(10) Patent No.: US 8,872,062 B2
(45) Date of Patent: Oct. 28, 2014

(54) LASER CUTTING PROCESS FOR FORMING STENTS

(75) Inventors: Li Chen, San Jose, CA (US); Travis Yribarren, Campbell, CA (US); Randolf Von Oepen, Los Altos, CA (US); Yu-Chun Ku, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 697 days.

(21) Appl. No.: 12/699,336

(22) Filed: Feb. 3, 2010

(65) Prior Publication Data

US 2010/0193483 A1 Aug. 5, 2010

Related U.S. Application Data

(60) Provisional application No. 61/149,630, filed on Feb. 3, 2009, provisional application No. 61/149,664, filed on Feb. 3, 2009, provisional application No. 61/149,667, filed on Feb. 3, 2009.

(51) Int. Cl.
*B23K 26/36* (2014.01)
*B23K 26/38* (2014.01)
*B23K 26/08* (2014.01)
*B23K 26/06* (2014.01)
*A61F 2/91* (2013.01)

(52) U.S. Cl.
CPC ............ *B23K 26/0626* (2013.01); *A61F 2/91* (2013.01); *B23K 26/365* (2013.01); *B23K 26/0823* (2013.01); *B23K 26/36* (2013.01); *B23K 26/38* (2013.01)

USPC .................................. 219/121.67; 219/121.61

(58) Field of Classification Search
CPC ................................ B23K 26/36; B23K 26/38
USPC .............. 219/121.61, 121.62, 121.67–121.72
See application file for complete search history.

(56) References Cited

U.S. PATENT DOCUMENTS

| | | |
|---|---|---|
| 4,387,952 A | 6/1983 | Slusher |
| 4,694,139 A | 9/1987 | Roder |
| 4,729,766 A | 3/1988 | Bergentz et al. |
| 4,733,665 A | 3/1988 | Palmaz |
| 4,736,381 A | 4/1988 | Eden et al. |
| 4,893,972 A | 1/1990 | Blaho |
| 4,947,022 A | 8/1990 | Ostroff et al. |
| 4,963,022 A | 10/1990 | Sommargren |

(Continued)

FOREIGN PATENT DOCUMENTS

| | | |
|---|---|---|
| EP | 0 221 570 A2 | 5/1987 |
| EP | 0 364 787 A1 | 4/1990 |

(Continued)

OTHER PUBLICATIONS

International Search Report dated Jul. 21, 2010.

(Continued)

*Primary Examiner* — Samuel M Heinrich
(74) *Attorney, Agent, or Firm* — Fulwider Patton LLP

(57) ABSTRACT

Systems and methods for improving the cutting efficiency and cut profile of stent strut is provided. A means for altering the energy distribution of a laser beam is provided, along with various ways of controlling a laser to provide for improved strut configurations are provided. A method for improved cutting speeds using a combination of laser sources is also provided.

3 Claims, 9 Drawing Sheets

(56) References Cited

U.S. PATENT DOCUMENTS

| | | |
|---|---|---|
| 4,994,071 A | 2/1991 | MacGregor |
| 5,049,723 A | 9/1991 | MacDonald |
| 5,059,211 A | 10/1991 | Stack et al. |
| 5,064,537 A | 11/1991 | Chupka et al. |
| 5,073,694 A | 12/1991 | Tessier et al. |
| 5,102,417 A | 4/1992 | Palmaz |
| 5,160,823 A | 11/1992 | Bennin et al. |
| 5,169,678 A | 12/1992 | Cole et al. |
| 5,222,617 A | 6/1993 | Gregory et al. |
| 5,306,286 A | 4/1994 | Stack et al. |
| 5,345,057 A | 9/1994 | Muller |
| 5,356,423 A | 10/1994 | Tihon et al. |
| 5,421,955 A | 6/1995 | Lau et al. |
| 5,514,154 A | 5/1996 | Lau et al. |
| 5,521,374 A | 5/1996 | Cray et al. |
| 5,569,295 A | 10/1996 | Lam |
| 5,591,197 A | 1/1997 | Orth et al. |
| 5,603,722 A | 2/1997 | Phan et al. |
| 5,605,696 A | 2/1997 | Eury et al. |
| 5,611,946 A | 3/1997 | Leong et al. |
| 5,656,186 A | 8/1997 | Mourou et al. |
| 5,720,894 A | 2/1998 | Neev et al. |
| 5,733,301 A * | 3/1998 | Forman ................... 606/192 |
| 5,759,192 A | 6/1998 | Saunders |
| 5,780,807 A | 7/1998 | Saunders |
| 5,824,049 A | 10/1998 | Regheb et al. |
| 5,841,099 A * | 11/1998 | Owen et al. ............ 219/121.69 |
| 5,854,805 A | 12/1998 | Reid et al. |
| 5,948,596 A | 9/1999 | Zhong et al. |
| 6,131,266 A | 10/2000 | Saunders |
| 6,160,240 A | 12/2000 | Momma et al. |
| 6,208,458 B1 | 3/2001 | Galvanauskas et al. |
| 6,214,115 B1 | 4/2001 | Taylor et al. |
| 6,229,829 B1 | 5/2001 | Yin |
| 6,245,103 B1 | 6/2001 | Stinson |
| 6,248,129 B1 | 6/2001 | Froix |
| 6,254,632 B1 | 7/2001 | Wu et al. |
| 6,281,262 B1 | 8/2001 | Shikinami |
| 6,324,195 B1 | 11/2001 | Suzuki et al. |
| RE37,585 E | 3/2002 | Mourou et al. |
| 6,369,355 B1 | 4/2002 | Saunders |
| 6,395,326 B1 | 5/2002 | Castro et al. |
| 6,411,636 B1 | 6/2002 | Ota et al. |
| 6,423,085 B1 | 7/2002 | Murayama et al. |
| 6,423,092 B2 | 7/2002 | Datta et al. |
| 6,448,733 B1 | 9/2002 | Joong et al. |
| 6,489,589 B1 | 12/2002 | Alexander |
| 6,517,888 B1 | 2/2003 | Weber |
| 6,517,889 B1 | 2/2003 | Jayaraman |
| 6,521,865 B1 | 2/2003 | Jones et al. |
| 6,531,679 B2 | 3/2003 | Heerman et al. |
| 6,537,480 B1 | 3/2003 | Becker et al. |
| 6,626,939 B1 | 9/2003 | Burnside et al. |
| 6,641,607 B1 | 11/2003 | Hossainy et al. |
| 6,643,426 B1 | 11/2003 | Alvarado et al. |
| 6,719,334 B1 | 4/2004 | Stinson |
| 6,878,901 B2 | 4/2005 | Johnson et al. |
| 6,927,359 B2 | 8/2005 | Kleine et al. |
| 7,077,859 B2 | 7/2006 | Sirhan et al. |
| 7,630,147 B1 * | 12/2009 | Kar et al. .................. 359/716 |
| 2002/0082679 A1 | 6/2002 | Sirhan et al. |
| 2002/0082685 A1 | 6/2002 | Sirhan et al. |
| 2002/0198589 A1 | 12/2002 | Leong |
| 2003/0050692 A1 | 3/2003 | Sirhan et al. |
| 2003/0052101 A1 | 3/2003 | Gu et al. |
| 2003/0139801 A1 | 7/2003 | Sirhan et al. |
| 2004/0002694 A1 * | 1/2004 | Pawlowski et al. ............... 606/4 |
| 2004/0059408 A1 | 3/2004 | Alvarado et al. |
| 2004/0127970 A1 | 7/2004 | Saunders et al. |
| 2004/0226922 A1 | 11/2004 | Flanagan |
| 2004/0230290 A1 | 11/2004 | Weber et al. |
| 2005/0033412 A1 | 2/2005 | Wu et al. |
| 2005/0070996 A1 | 3/2005 | Dinh et al. |
| 2005/0087520 A1 | 4/2005 | Wang et al. |
| 2006/0033240 A1 | 2/2006 | Weber et al. |
| 2006/0041102 A1 | 2/2006 | Hossainy et al. |
| 2006/0054604 A1 | 3/2006 | Saunders |
| 2007/0145024 A1 * | 6/2007 | Salama et al. ........... 219/121.71 |
| 2007/0151961 A1 | 7/2007 | Klaine et al. |
| 2008/0269870 A1 | 10/2008 | Ruuttu et al. |

FOREIGN PATENT DOCUMENTS

| | | |
|---|---|---|
| EP | 0 372 789 A3 | 6/1990 |
| EP | 0 421 729 A2 | 4/1991 |
| EP | 0 540 290 A2 | 5/1993 |
| EP | 0 541 443 A1 | 5/1993 |
| EP | 0 562 150 A1 | 9/1993 |
| EP | 0 624 421 A2 | 11/1994 |
| EP | 0 662 307 A1 | 7/1995 |
| EP | 0 679 373 A2 | 11/1995 |
| EP | 0 714 641 A2 | 6/1996 |
| EP | 1 466 634 A1 | 10/2004 |
| GB | 2 070 490 A | 9/1981 |
| JP | 61169188 | 7/1986 |
| JP | 5-285898 | 11/1993 |
| WO | 92/06734 | 4/1992 |

OTHER PUBLICATIONS

C.H. Fan et al., "Plasma Absorption of Femtosecond Laser Pulses in Dielectrics," Journal of Heat Transfer, Apr. 2002, vol. 124, pp. 275-283.

Brochure: Industrial Strength Laser Marking: Turning Photonix into Dollars, printed by Excel/Control Laser, Inc.

Brochure: Anomatic TM II Positioning Controller, printed by Anorad Corporation (undated).

J.Sun et al., "Inert gas beam delivery for ultrafast laser micromachining at ambient pressure," Journal of Applied Physics, Jun. 13, 2001, vol. 89, No. 12, pp. 8219-8224.

* cited by examiner

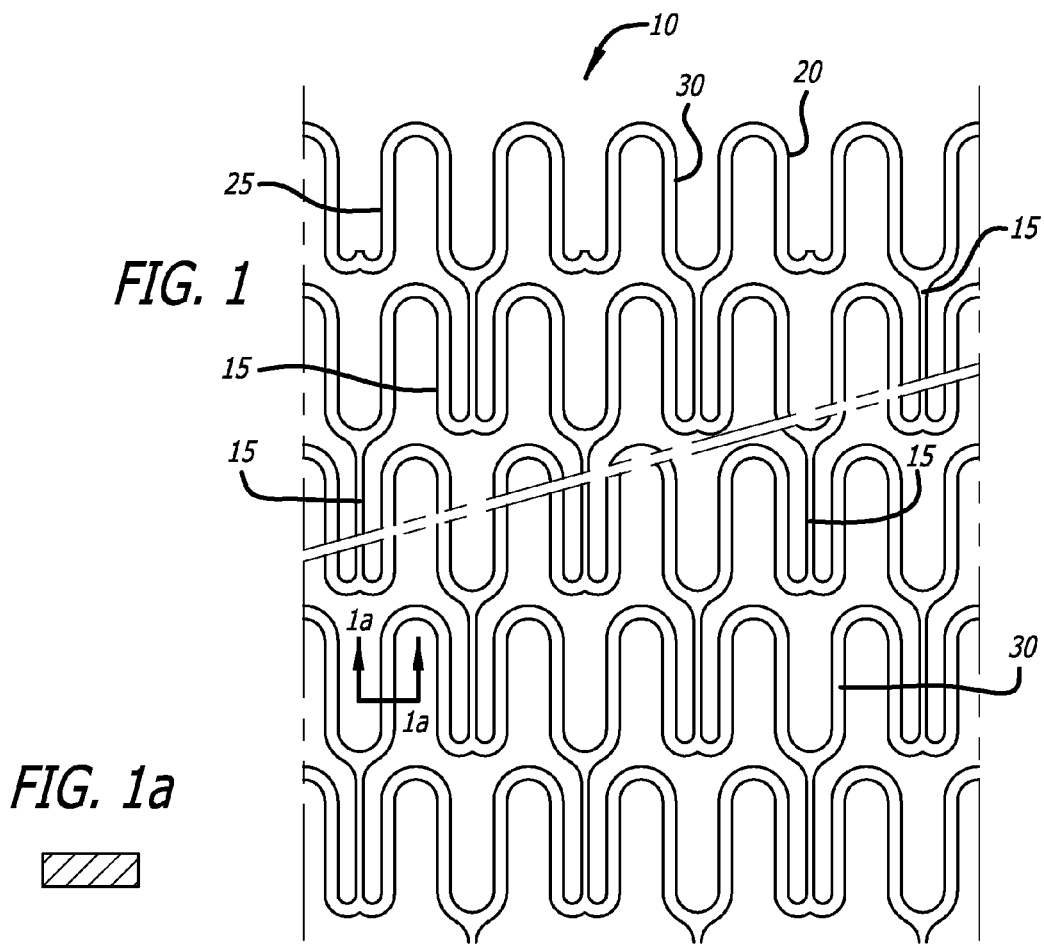
FIG. 1
FIG. 1a
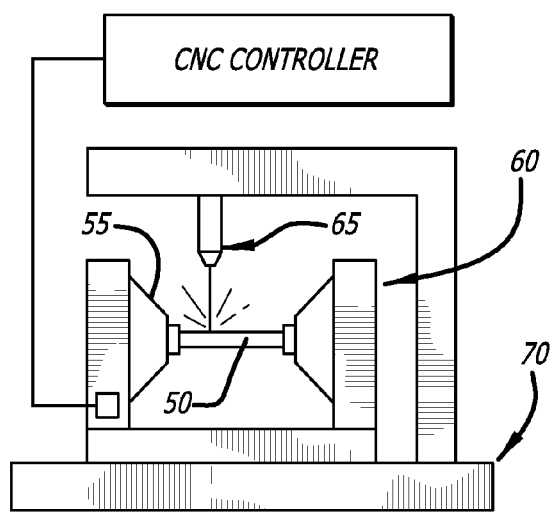
FIG. 2

LASER CUTTING PROCESS FOR FORMING STENTS

CROSS-REFERENCES TO RELATED APPLICATIONS

This application claims priority from U.S. Provisional Application No. 61/149,630, filed Feb. 3, 2009 and U.S. Provisional Application No. 61/149,664, filed Feb. 3, 2009 and U.S. Provisional Application No. 61/149,667, filed Feb. 3, 2009 incorporated by reference in its entirety.

This application is also related to U.S. application Ser. No. 12/699,336 entitled LASER CUTTING SYSTEM, filed Feb. 3, 2010, and U.S. application Ser. No. 12/699,391 entitled MULTIPLE BEAM LASER SYSTEM FOR FORMING STENTS, filed Feb. 3, 2010, now U.S. Pat. No. 8,461,478.

BACKGROUND

1. Field of the Invention

The present invention relates generally to implantable medical devices and to a method for manufacturing implantable medical devices. These implantable medical devices may also be capable of retaining therapeutic materials and dispensing the therapeutic materials to a desired location of a patient's body. More particularly, the present invention relates to a method for forming the structure of a stent or intravascular or intraductal medical device.

2. General Background and State of the Art

In a typical percutaneous transluminal coronary angioplasty (PTCA) for compressing lesion plaque against the artery wall to dilate the artery lumen, a guiding catheter is percutaneously introduced into the cardiovascular system of a patient through the brachial or femoral arteries and advanced through the vasculature until the distal end is in the ostium. A dilatation catheter having a balloon on the distal end is introduced through the catheter. The catheter is first advanced into the patient's coronary vasculature until the dilatation balloon is properly positioned across the lesion.

Once in position across the lesion, a flexible, expandable, preformed balloon is inflated to a predetermined size at relatively high pressures to radially compress the atherosclerotic plaque of the lesion against the inside of the artery wall and thereby dilate the lumen of the artery. The balloon is then deflated to a small profile, so that the dilatation catheter can be withdrawn from the patient's vasculature and blood flow resumed through the dilated artery. While this procedure is typical, it is not the only method used in angioplasty.

In angioplasty procedures of the kind referenced above, restenosis of the artery often develops which may require another angioplasty procedure, a surgical bypass operation, or some method of repairing or strengthening the area. To reduce the likelihood of the development of restenosis and strengthen the area, a physician can implant an intravascular prosthesis, typically called a stent, for maintaining vascular patency. In general, stents are small, cylindrical devices whose structure serves to create or maintain an unobstructed opening within a lumen. The stents are typically made of, for example, stainless steel, nitinol, or other materials and are delivered to the target site via a balloon catheter. Although the stents are effective in opening the stenotic lumen, the foreign material and structure of the stents themselves may exacerbate the occurrence of restenosis or thrombosis.

A variety of devices are known in the art for use as stents, including expandable tubular members, in a variety of patterns, that are able to be crimped onto a balloon catheter, and expanded after being positioned intraluminally on the balloon catheter, and that retain their expanded form. Typically, the stent is loaded and crimped onto the balloon portion of the catheter, and advanced to a location inside the artery at the lesion. The stent is then expanded to a larger diameter, by the balloon portion of the catheter, to implant the stent in the artery at the lesion. Typical stents and stent delivery systems are more fully disclosed in U.S. Pat. No. 5,514,154 (Lau et al.), U.S. Pat. No. 5,507,768 (Lau et al.), and U.S. Pat. No. 5,569,295 (Lam et al.).

Stents are commonly designed for long-term implantation within the body lumen. Some stents are designed for non-permanent implantation within the body lumen. By way of example, several stent devices and methods can be found in commonly assigned and common owned U.S. Pat. No. 5,002,560 (Machold et al.), U.S. Pat. No. 5,180,368 (Garrison), and U.S. Pat. No. 5,263,963 (Garrison et al.).

Intravascular or intraductal implantation of a stent generally involves advancing the stent on a balloon catheter or a similar device to the designated vessel/duct site, properly positioning the stent at the vessel/duct site, and deploying the stent by inflating the balloon which then expands the stent radially against the wall of the vessel/duct. Proper positioning of the stent requires precise placement of the stent at the vessel/duct site to be treated. Visualizing the position and expansion of the stent within a vessel/duct area is usually done using a fluoroscopic or x-ray imaging system.

Although PTCA and related procedures aid in alleviating intraluminal constrictions, such constrictions or blockages reoccur in many cases. The cause of these recurring obstructions, termed restenosis, is due to the body's immune system responding to the trauma of the surgical procedure. As a result, the PTCA procedure may need to be repeated to repair the damaged lumen.

In addition to providing physical support to passageways, stents are also used to carry therapeutic substances for local delivery of the substances to the damaged vasculature. For example, anticoagulants, antiplatelets, and cytostatic agents are substances commonly delivered from stents and are used to prevent thrombosis of the coronary lumen, to inhibit development of restenosis, and to reduce post-angioplasty proliferation of the vascular tissue, respectively. The therapeutic substances are typically either impregnated into the stent or carried in a polymer that coats the stent. The therapeutic substances are released from the stent or polymer once it has been implanted in the vessel.

In the past, stents have been manufactured in a variety of manners, including cutting a pattern into a tube that is then finished to form the stent. The pattern can be cut into the tube using various methods known in the art, including using a laser.

Laser cutting of the stent pattern initially utilized lasers such as the conventional Nd:YAG laser, configured either at its fundamental mode and frequency, or where the frequency of the laser light was doubled, tripled, or even quadrupled to give a light beam having a desired characteristic to ensure faster and cleaner cuts.

Recently, lasers other than Nd:YAG lasers have been used, such as solid-state lasers that operate in the short pulse pico-second and femto-second domains. These lasers provide improved cutting accuracy, but cut more slowly than conventional lasers such as the long pulse Nd:YAG laser.

The intensity of the light beam created by either conventional long pulse or short pulse lasers such as pico-second and femto-second lasers has a Gaussian distribution. A laser beam having a Gaussian intensity distribution results in a beam having higher energy intensity at the center of the beam spot, with reduced energy as a function of distance from the center of the beam spot. This results in a tapered cut when the laser beam cuts through a material. In other words, the cut on the topside of the material is wider than the exit of the laser beam through the bottom side of the material.

When a laser having a Gaussian intensity distribution is used to cut a stent strut the resulting tapered edge causes difficulty in achieving overall dimensional stability after electrochemical polishing. The tapered edge shape may also not be ideal in carrying out its function when the stent is implanted in a vessel, as the tapered strut may not be ideal in opposing the vessel wall.

An additional problem with prior art systems that typically have used lasers that generate long laser pulses with durations in the microsecond range is that this type of laser removes material using a mostly thermal process, with some degree of evaporation of tubing material. In contrast, new lasers operate in the range of 10 pico-seconds ($10 \times 10^{-12}$ seconds) or shorter for stent cutting, and remove material by way of ablation rather than a thermal process.

The thermal process using long laser pulses can result in molten material and slag, which may be redeposited upon the stent surfaces, as well as surrounding surfaces of the cutting equipment. The thermal process of the long pulse laser may also result in production of a heat-affected zone in the stent tubing material. This heat-affected zone, which occurs frequently when the stent tube is cut by the long pulse laser in the presence of certain reactive gases such as oxygen can result in embrittlement of the stent material and thus decreases mechanical performance of the stent material. In contrast, the short pulses of a pico-second or femto-second laser removes material primarily through ablation which results in minimal thermal damage and a reduction in the amount of slag produced during the ablation process.

What has been needed, and heretofore unavailable, is an efficient and cost-effective laser cutting system that provides for improved cutting speeds and cut profiles. The present invention satisfies these, and other needs.

SUMMARY OF THE INVENTION

In one aspect, the present invention is embodied in a system that utilizes a laser beam that has been shaped using a shaping module to modify the intensity profile of the laser beam. In other aspects, the shaped laser beam has a more even intensity profile across the relevant beam diameter than is typically delivered by a non-shaped laser beam having a Gaussian profile. Control over such a shaped laser beam produces cleaner surfaces and faster fabrication times. Use of a shaped beam having an alternative energy profile may also result in improved stent characteristics that are advantageous to stent performance and function. For example, shaped laser beam profiles may result in a steeper stent sidewall than is obtainable using a laser beam with a Gaussian intensity distribution, which may improve manufacturability and performance of the stent. Moreover, use of shaped laser beams formed in accordance with the various aspects of the present invention may also result in improved stent cutting speeds, optical characteristics, and drug retention characteristics. It will be understood that the laser beam shaping technology described herein can be used for forming other medical device components, particularly where improved edge surfaces or component fits and the like are required. For example, such a system could be used to produce parts of a guidewire or catheter device. It may also be used to provide for precise machining of pacemaker components.

In yet another aspect, the system of the present invention includes a laser cutting system for cutting a stent pattern into a stent, comprising a laser for producing a laser beam; a laser-shaping module capable of altering the intensity profile of the laser beam; and, a collimating lens.

In still another aspect, the present invention includes a method from shaping a laser beam for cutting a stent pattern into a stent, comprising providing a laser beam having a first intensity distribution; and re-mapping the first intensity distribution of the laser beam to a second intensity distribution.

In still another aspect, the present invention provides a laser cutting process that enables greater control over the shape of the stent strut. The improved dimensional control is achieved in one aspect by offsetting the path of a laser beam from the central axis of a stent tube. By offsetting the laser from the central axis of the tube, the typical taper resulting from use of a Gaussian laser beam may be virtually eliminated, producing a stent strut with a much more rectangular shape.

In another aspect, more than one laser beam can be used, with the more than one laser beams offset from the central axis of the tube. In such an arrangement, the first laser beam may cut a perpendicular stent wall on one stent strut while a second beam, offset from both the central axis of the tube and the cutting axis of the first laser beam, is used to cut a second stent wall.

In yet another aspect, a single laser beam can be used to cut both sides of a stent strut to result in a rectangular strut. The laser beam is moved from a first position having a first offset angle to a second position having a second offset angle so that the walls of each stent strut may be cut by the laser. In an alternative aspect, the stent tubing may be moved relative to the laser to accomplish the same result. In still another aspect, both the laser and the tube may be moved simultaneously to one another to achieve the same effect.

In a further aspect, the present invention includes a method for cutting a stent pattern into a tube, comprising: remapping the intensity distribution of a laser beam to a non-Gaussian intensity distribution; and applying the non-Gaussian intensity beam to a tube to remove at least a portion of a wall thickness of the tube.

In yet a further aspect, applying the beam to the tube includes exposing the tube to multiple passes of the laser beam. In a still further aspect, remapping includes providing a non-Gaussian intensity distribution to the laser beam, the non-Gaussian intensity distribution having at least one characteristic resulting in removing material from the wall of the tube in a selected configuration. In still another aspect, the selected configuration includes forming indentations on a surface of the tube.

In yet another aspect, the present invention includes a system for cutting a stent pattern into a tube, comprising: a tube mounted in a fixture, the tube having a central axis; a first laser beam for cutting a portion of a pattern into the tube, the first laser and tube arranged relative to one another such that the laser beam is directed to a surface of the tube on an axis that is offset from the central axis of the tube; a second laser beam for cutting a second portion of the pattern in the tube, the second laser beam and tube arranged relative to one another such that the laser beam is directed to the surface of the tube on an axis that is offset from the central axis of the tube and the axis of the first laser beam.

In yet another aspect, the present invention includes a system for cutting stent patterns into a tube, comprising: a tube mounted in a fixture, the tube having a central axis; a laser for providing a laser beam for cutting a portion of a pattern into the tube, the laser beam and tube moveable with respect to one another such that the laser beam is oriented in a first position relative to the tube and the beam directed to a first surface of the tube on an axis that is offset from the central axis.

In another aspect, the laser beam or tube are moved to a second position such that the laser beam is directed to a second surface of the tube, the axis of the laser beam being offset to the central axis of the tube by an offset different from the offset used to cut the first surface of the tube. In yet another aspect, a rectangular strut is produced.

In still another aspect, the present invention includes a system and method for cutting patterns into a tube using a series of laser passes to cut the pattern. In one aspect, the system makes a first cut of the pattern to a depth of less than the wall thickness of the tube using a long pulse laser. One or more additional passes are then performed using a short pulse laser, such as a pico-second laser, to complete the cut. In yet another aspect, a long wavelength pico-second laser is used to make the first cut, then a short wavelength pico-second laser is used to complete the cut.

In another aspect, the present invention includes systems and methods where a long pulse laser and a short pulse laser are mounted to a common base and the tube is passed first below the long pulse laser and then below the short pulse laser in a continuous cutting process.

In yet another aspect, the first cutting operation is carried out on one laser cutting station and then the tube is moved to a second cutting station where the cutting of the stent patter is completed by a short pulse laser.

In still another aspect, the present invention includes use of a laser capable of being configured to operate in a long pulse mode to make a first cut and then being capable of being reconfigured to operate in a short pulse mode to make a second cut.

In yet another aspect, the present invention includes a method of cutting a stent pattern into a tube, comprising: mounting a tube is a fixture; cutting a pattern into the tube to a depth less than a wall thickness of the tube using a long pulse laser, the laser and fixture controlled by a computer to provide for relative motion between the long pulse laser and the tube; and cutting the pattern into the tube to a depth greater than the wall thickness of the tube using a short pulse laser, the short pulse laser and fixture controlled by the computer to provide for relative motion between the short pulse laser and the tube.

In another aspect, the tube may be moved to a different location before the pattern is cut by the short pulse laser.

In still another aspect, the long pulse laser and the short pulse laser and fixture are mounted on a common base.

In a further aspect, the present invention also includes a method for cutting a stent pattern into a tube, comprising: mounting a tube is a fixture; configuring a laser to operate in a long pulse mode; cutting a pattern into the tube to a depth less than a wall thickness of the tube using the laser operating in the long pulse mode, the laser and fixture controlled by a computer to provide for relative motion between the laser and the tube; configuring the laser to operate in a short pulse mode; and cutting the pattern into the tube to a depth greater than the wall thickness of the tube using the laser operating in the short pulse mode, the laser and fixture controlled by the computer to provide for relative motion between the laser and the tube.

In a still further aspect, the present invention includes a method for a stent pattern having multiple cells into a tube, comprising mounting a tube in a fixture, cutting each cell of the pattern into the tube using a laser, completing the cutting of each cell before beginning cutting of the next cell until all of the cells are cut.

Other features and advantages of the invention will become apparent from the following detailed description, taken in conjunction with the accompanying drawings, which illustrate, by way of example, the features of the invention.

BRIEF DESCRIPTION OF THE DRAWINGS

FIG. 1 is a partial view of a stent showing various elements of a stent pattern.

FIG. 1a is a cross-sectional view of a portion of one of the elements of the stent pattern.

FIG. 2 is a side view of a typical arrangement of a computer controlled cutting station for cutting stent patterns into tubing using a laser beam.

DETAILED DESCRIPTION OF THE PREFERRED EMBODIMENTS

Figure 3:
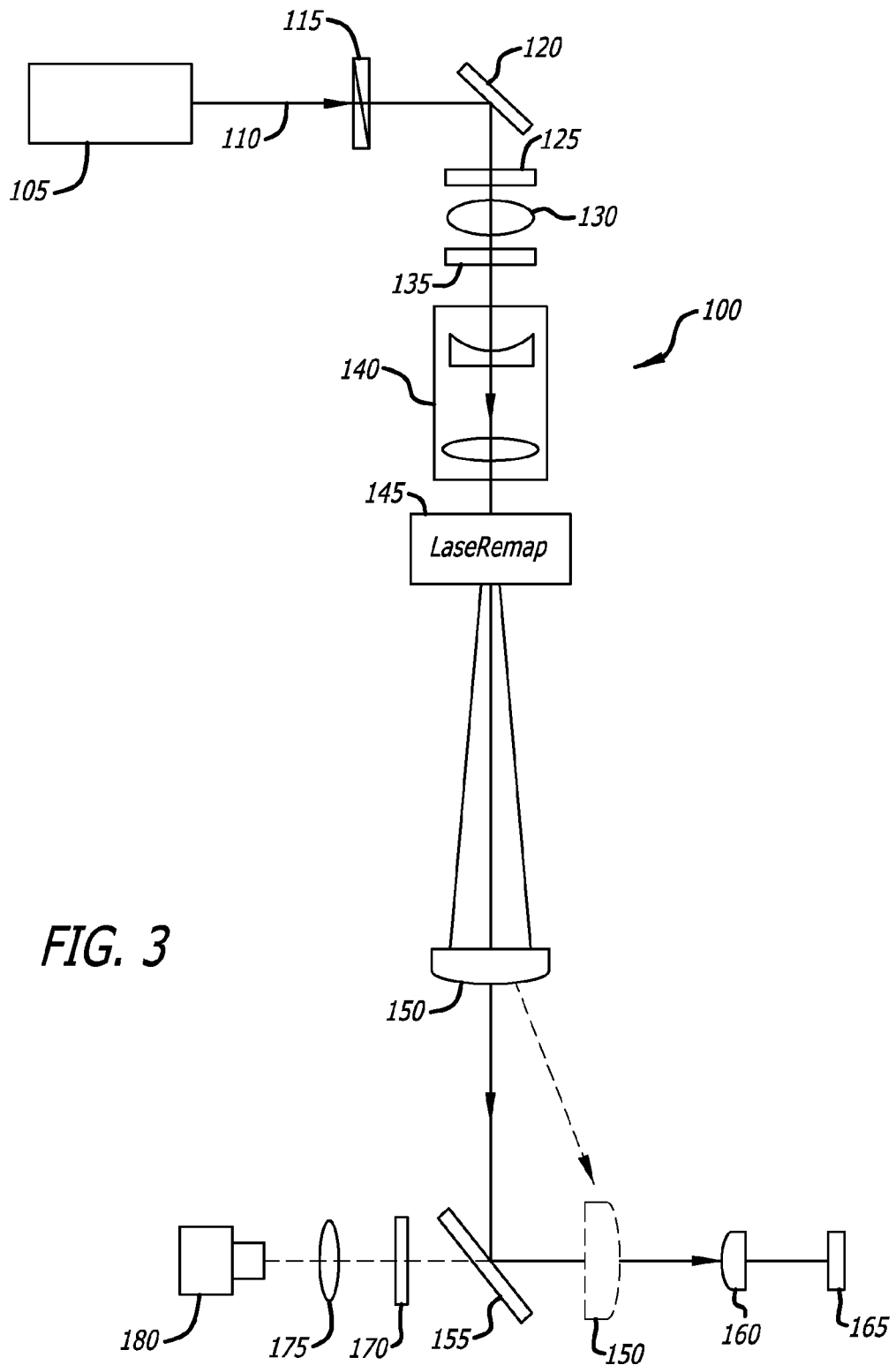
FIG. 3 is a graphical illustration of an embodiment of layout of a laser system incorporating aspects of the present invention.

FIG. 1 is an enlarged perspective view of a stent 10 illustrating an exemplary stent pattern and showing the placement of interconnecting elements 15 between adjacent radially expandable cylindrical elements. Each pair of the interconnecting elements 15 on one side of a cylindrical element are preferably placed to achieve maximum flexibility for a stent. In the embodiment shown in FIG. 1, the stent 10 has three interconnecting elements 15 between adjacent radially expandable cylindrical elements which are 120 degrees apart. Each pair of interconnecting elements 15 on one side of a cylindrical element are offset radially 60 degrees from the pair on the other side of the cylindrical element. The alternation of the interconnecting elements results in a stent which is longitudinally flexible in essentially all directions. Various configurations for the placement of interconnecting elements are possible. However, as previously mentioned, all of the interconnecting elements of an individual stent should be secured to either the peaks or valleys of the undulating structural elements in order to prevent shortening of the stent during the expansion thereof.

The number of undulations may also be varied to accommodate placement of interconnecting elements 15, for example, at the peaks of the undulations or along the sides of the undulations as shown in FIG. 1.

As best observed in FIG. 1, cylindrical elements in this exemplary embodiment are shown in the form of a serpentine pattern. As previously mentioned, each cylindrical element is connected by interconnecting elements 15. The serpentine pattern is made up of a plurality of U-shaped members 20, W-shaped members 25, and Y-shaped members 30, each having a different radius so that expansion forces are more evenly distributed over the various members.

The afore-described illustrative stent 10 and similar stent structures can be made in many ways. However, the preferred method of making the stent is to cut a thin-walled tubular member, such as, for example, stainless steel tubing to remove portions of the tubing in the desired pattern for the stent, leaving relatively untouched the portions of the metallic tubing which are to form the stent. In accordance with the invention, it is preferred to cut the tubing in the desired pattern by means of a machine-controlled laser, as exemplified schematically in FIG. 2.

The tubing may be made of suitable biocompatible material such as, for example, stainless steel. The stainless steel tube may be Alloy type: 316L SS, Special Chemistry per ASTM F138-92 or ASTM F139-92 grade 2. Special Chemistry of type 316L per ASTM F138-92 or ASTM F139-92 Stainless Steel for Surgical Implants. Other biomaterials may also be used, such as various biocompatible polymers, co-polymers or suitable metals, alloys or composites that are capable of being cut by a laser.

Another example of materials that can be used for forming stents is disclosed within U.S. application Ser. No. 12/070, 646, the subject matter of which is intended to be incorporated herein in its entirety, which application discloses a high strength, low modulus metal alloy comprising the following elements: (a) between about 0.1 and 70 weight percent Niobium, (b) between about 0.1 and 30 weight percent in total of at least one element selected from the group consisting of Tungsten, Zirconium and Molybdenum, (c) up to 5 weight percent in total of at least one element selected from the group consisting of Hafnium, Rhenium and Lanthanides, in particular Cerium, (d) and a balance of Tantalum The alloy provides for a uniform beta structure, which is uniform and corrosion resistant, and has the ability for conversion oxidation or nitridization surface hardening of a medical implant or device formed from the alloy. The tungsten content of such an alloy is preferably between 0.1 and 15 weight percent, the zirconium content is preferably between 0.1 and 10 weight percent, The molybdenum content is preferably between 0.1 and 20 weight percent and the niobium content is preferably between 5 and 25 weight percent.

The stent diameter is very small, so the tubing from which it is made must necessarily also have a small diameter. Typically the stent has an outer diameter on the order of about 0.06 inch in the unexpanded condition, the same outer diameter of the tubing from which it is made, and can be expanded to an outer diameter of 0.1 inch or more. The wall thickness of the tubing is about 0.003 inch or less.

Referring now to FIG. 2, the tubing 50 is put in a rotatable collet fixture 55 of a machine-controlled apparatus 60 for positioning the tubing 50 relative to a laser 65. According to machine-encoded instructions, the tubing 50 is rotated and moved longitudinally relative to the laser 65 which is also machine-controlled. The laser selectively removes the material from the tubing and a pattern is cut into the tube. The tube is therefore cut into the discrete pattern of the finished stent.

The process of cutting a pattern for the stent into the tubing is automated except for loading and unloading the length of tubing. Referring again to FIG. 2, it may be done, for example, using a CNC-opposing collet fixture 55 for axial rotation of the length of tubing, in conjunction with a CNC X/Y table 70 to move the length of tubing axially relatively to a machine-controlled laser as described. Alternatively, the collet fixture may hold the tube at only one end, leaving the opposite end unsupported. The entire space between collets can be patterned using the laser. The program for control of the apparatus is dependent on the particular configuration used and the pattern to be cut by the laser.

In one embodiment, the invention includes an apparatus and method for laser cutting a stent with a shaped laser beam to produce beneficial stent characteristics. The embodiment utilizes a laser beam-shaping module to modify the intensity profile of a laser beam. The modified intensity profile results in beneficial stent characteristics, such as better-formed sidewalls with a cleaner cut surface. Using a modified intensity profile, the stent surface may also be modified by using various beam shapes to produce additional benefits, such as optical or coating retention improvements.

Referring now to FIG. 3, an embodiment of an exemplary pico-second laser system optical layout 100 is shown. In this embodiment, a pico-second laser 105 generates a laser beam 110 having a Gaussian intensity distribution that is then is directed through a shutter 115 onto a mirror 120. Although shown in this exemplary embodiment, one skilled in the art will appreciate that mirror 120 is not necessary if the design requirements of the system allow the laser and other optical components to be arranged in a linear fashion.

The reflected beam then passes through a half wave plate 125, polarizer 130 and quarter wave plate 135, before entering a beam expander 140. Beam expander 140 is used to control the spot size of the beam. The laser beam 110 exits the beam expander and enters a laser beam shaper, such as a LaseRemap, manufactured by Lambda Research Inc. Within the beam shaper, the Gaussian intensity distribution of the laser beam is transformed to an Airy pattern. Passing through a collimating lens 150, the collimated Airy pattern laser beam may then be reflected by a mirror 155, although mirror 155 is not necessary to the performance of the invention, the inclusion of such a mirror may be beneficial in compacting the optical arrangement to reduce the size of the optical train. The collimated Airy pattern laser beam undergoes a Fourier transform through a focusing lens 160, resulting in a focused beam intensity profile that appears similar to a top hat. This beam profile is then directed onto the work piece 165.

The modified laser beam is then directed toward a work piece, for example, a piece of tubing to be cut into a stent. Alternatively, mirror 155 may also be partially transmissive, allowing the cutting of the work piece 165 to be observed by a camera or other view device 180 that views the work piece through a filter and lens assembly 170, 175.

In an alternative embodiment, collimating lens 150 may be located after the beam 110 is reflected by mirror 155. This arrangement may be advantageous depending on the overall layout of the optical system and sizing requirements of the system.

The laser beam shaper may typically be formed of two fused silica plano-convex aspheric lenses, arranged with the convex surfaces facing each other. In this arrangement, the device takes the general form of a Keplerian telescope, with a radially varying magnification. Because of the optics of the beam shaper, the Gaussian intensity distribution of the laser beam is modified to a non-Gaussian distribution, as will be discussed below in more detail. The distance between the two lenses of the beam shaper may be changed to generate a variety of beam intensity profiles. However, for reasons that will be discussed in more detail below, an arrangement where the beam intensity profile takes the general form of a "top hat" is generally preferred.

The focal length of the collimator has an effect on the final spot size of the shaped laser beam. However, the final focal spot size of the shaped beam is limited mainly by the beam shaper.

Further details of a beam-shaping module in accordance with aspects of the present invention are included in "Lambda Research Optics, Inc."; "Aspheric Laser Beam Reshaper Applications Guide;" by C. Michael Jefferson and John A. Hoffnagel; "Transformation of a Gaussian Laser Beam to an Airy Pattern for use in Focal Plane Intensity Shaping Using Diffractive Optics," by Kurt Kanzler; and U.S. Pat. No. 6,975,458 issued to Kanzler entitled "Method and Apparatus for Transformation of a Gaussian Laser Beam to Far Field Diffraction Pattern." The subject of each of these references is intended to be incorporated herein in their entirety.

Figure 4:
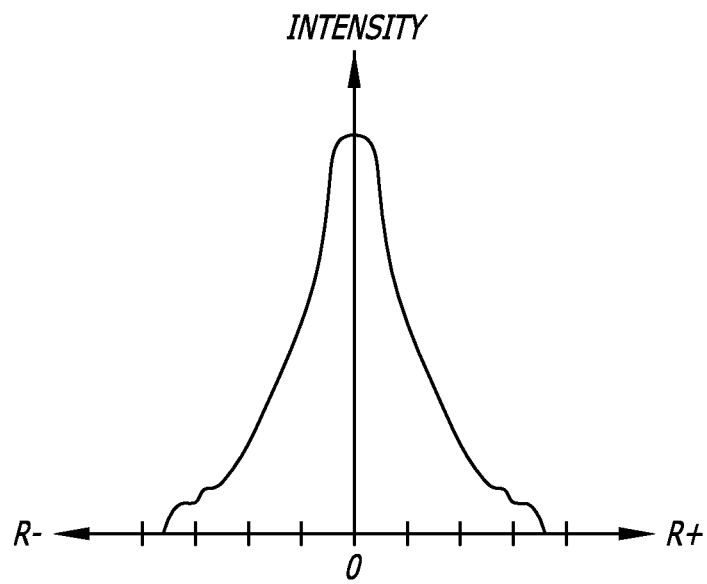
FIG. 4 is a graphical illustration of a laser beam intensity profile of a standard laser showing a typical Gaussian profile.

FIG. 4 depicts a typical Gaussian laser beam intensity profile for a laser that has not undergone shaping. As can be seen in FIG. 4, the intensity towards the center of the beam is much greater than the intensity at the edges of the beam spot. This drop off in intensity occurs quite rapidly as a function of distance from the beam center. As a result, the cut profile produced by directing this laser beam toward a piece of material has a similarly varied curvature, as the rate of material removal due to ablation is dependent on the applied laser beam intensity.

Figure 5:
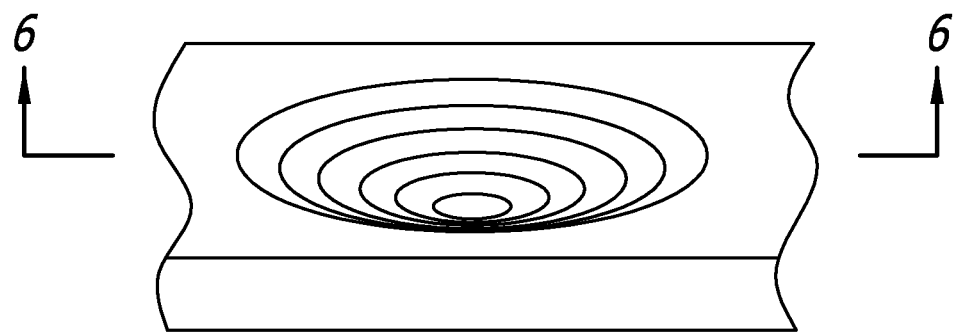
FIG. 5 is a prospective view illustrating a typical ablation of a surface using a laser having the beam profile of FIG. 4.
Figure 6:
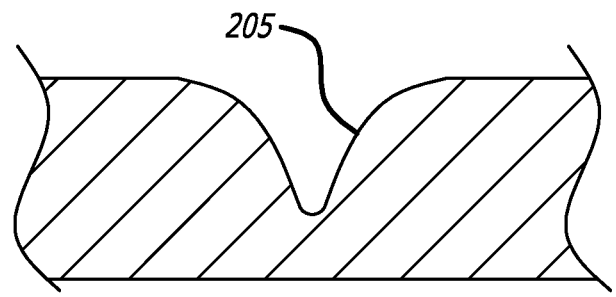
FIG. 6 is a cross-sectional view of the surface of FIG. 5 showing a conical profile of the cut similar in shape to the Gaussian profile of FIG. 4.

An example of the cut profile produced by directing a laser beam with Gaussian intensity profile is shown in FIG. 5. A Gaussian intensity profile as depicted in FIG. 4 typically produces a generally conical profile with the central portion of the cut area being deeper than the edges of the cut area. As one skilled in the art would expect, the profile of the cut area is similar to the intensity profile of the laser beam. This is further illustrated by FIG. 6, which shows a cross-section of a cut profile produced by a laser beam having a Gaussian intensity profile. One important aspect to be noted from FIG. 6 is that the cut profile shows sidewalls 205 having a positive taper, that is, the area of the cut on the top of the work piece where the laser beam is directed is larger than at the bottom of the of the cut.

Figure 9:
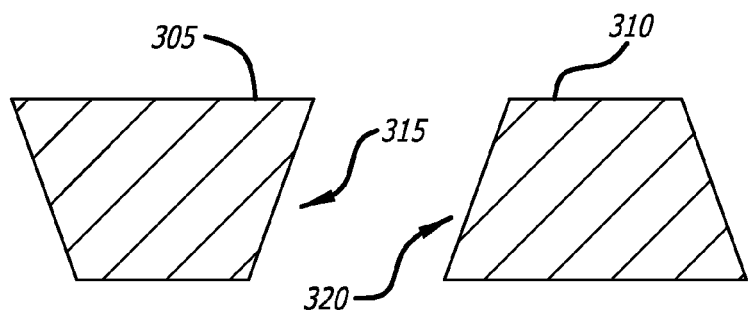
FIG. 9 is a cross-sectional view of stent struts of the stent pattern of FIG. 1 cut by a laser beam having the Gaussian intensity profile of FIG. 4.

The effect of such a Gaussian intensity profile on a cut stent can be seen by referring to FIG. 9. FIG. 9 shows a cross-section of struts 305, 310 of a stent cut with a laser beam having a Gaussian intensity profile. The sidewalls 315, 320 of the stent struts 305, 310 are sloped, as would be expected from the cut profile shown in FIG. 6. This results in a stent strut having a non-uniform shape, such as, for example, and as illustrated in FIG. 6, having a top side that is larger that the side directly opposite.

Figure 7:
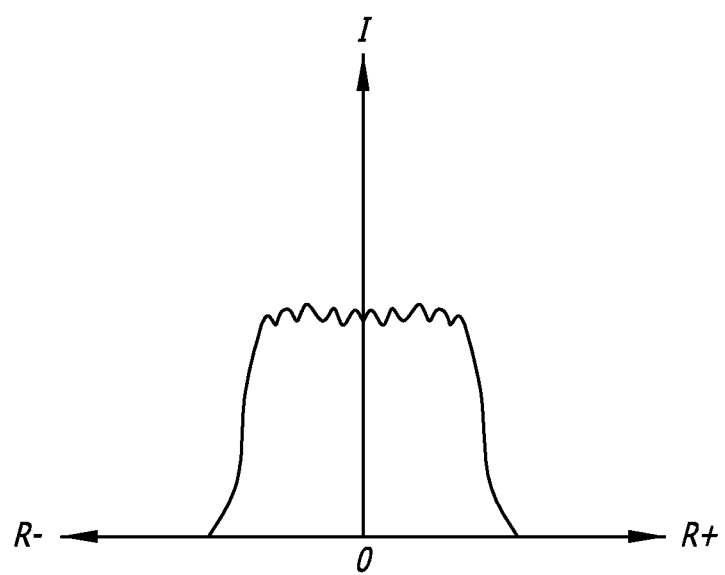
FIG. 7 is a graphical illustration of a laser beam intensity profile of a laser beam shaped in accordance with aspects of the present invention.

FIG. 7 depicts a laser beam intensity profile for laser beam that has undergone reshaping in accordance with the principles of the present invention. This profile illustrates one example of a beam generated by the system of FIG. 3 wherein the beam shaper is adjusted to produce a beam intensity having what is called in the art a "top hat" or "flat top" profile. In such an intensity profile, the intensity of the beam is relatively constant across the diameter of the laser beam, unlike the intensity profile of the Gaussian beam depicted in FIG. 4. Accordingly, the edges of the shaped beam have approximately the same intensity as the center of the beam, providing reduced intensity drop off at the beam's edge.

Figure 8:
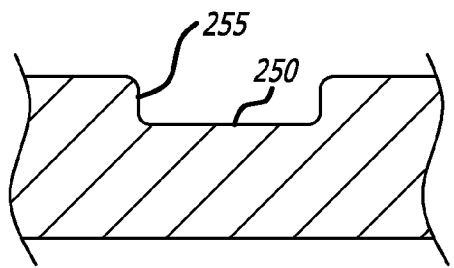
FIG. 8 is a cross-sectional view of an ablation profile in a surface that was created using a laser beam having the beam intensity profile of FIG. 7.

FIG. 8 is a cross-sectional view of a tube wall that has been cut using a shaped beam having an intensity profile similar to the profile shown in FIG. 7. The flat top profile of the shaped beam creates a cut with a relatively uniform depth across the cut diameter. Further, due to the uniformity of the beam intensity across the beam diameter, the edges 255 of the cut are much steeper, that is, having less taper, as compared to the cut produced by a Gaussian beam depicted in FIG. 9.

Figure 10:
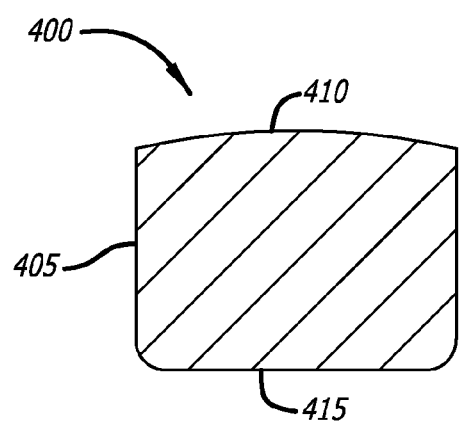
FIG. 10 is a cross-sectional view of a stent strut cut by a shaped laser beam having an intensity profile similar to that shown in FIG. 8.

FIG. 10 shows a stent strut 400 cut with a laser beam having a flat top intensity profile as is shown in FIG. 7. It is quickly apparent that the stent strut 400 has a much steeper sidewall 405. This steep sidewall 405 is preferred over tapered sidewalls such as are shown in FIG. 9 because the resulting overall strut geometry is much more uniform, as illustrated by the similar widths of strut top 410 and strut bottom 415. Sloped or tapered sidewalls are disadvantageous in that they produce non-uniform geometries that can affect stent performance. Also, manufacturing processes such as electro-polishing and sandblasting are better suited to non-sloped stent struts because they will produce more desirable strut geometries.

The shape of the beam intensity profile affects the distribution of energy across the surface of the material being cut, which has manufacturing and as-cut geometry implications. A Gaussian beam profile inherently applies much more energy to the center of the beam spot when such a laser beam is cutting material. As a result, the center portion of the cut material will be heated much more quickly than the edges of the cut material. This is an inefficient energy distribution since the edges of the cut area will be melted/ablated using a relatively low intensity of the laser beam, increasing the total time necessary to cut through the tubing wall. In contrast, a beam having a top hat or flat intensity profile shaped in accordance with principles of the present invention applies energy uniformly across the surface to be cut, providing more efficient delivery of energy to the entire cut area and resulting in faster fabrication times.

The intensity distribution within the beam cutting area may also affect the quantity and flow characteristics of slag/debris that is formed during the laser cutting process. It is believed by the inventors that more slag/debris more is formed with a laser beam having a Gaussian intensity profile then with a shaped laser beam having a flat top intensity profile. Also, the slag/debris formed with the Gaussian laser beam may flow in such a way that a significant amount of slag remains on a stent strut after cutting. This is disadvantageous in that such slag/debris contamination requires additional time and resources for post-processing of the as-cut stent.

Figure 11:
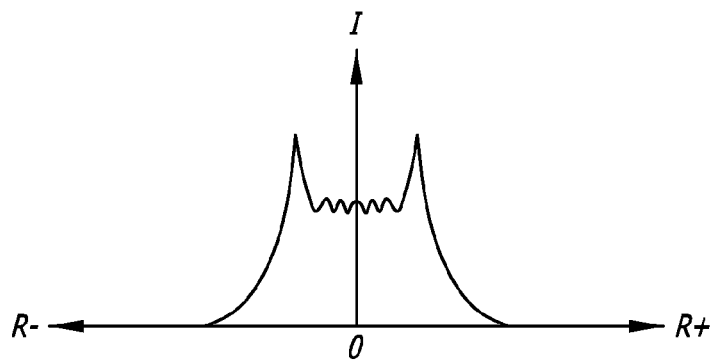
FIG. 11 is a graphical illustration of a laser beam intensity profile of a laser beam shaped in accordance with an alternative embodiment of the present invention.

Shaping the laser beam in accordance with the present invention may result in other useful beam shapes. An example of such an alternative beam shape is shown in FIG. 11. In this example, the beam shaper is adjusted to provide a laser beam having an intensity profile where the beam is more intense toward the outer beam edges. Such an intensity profile appears to have "ears." When such a shaped beam is applied to a material, the cut profile resembles that shown in FIG. 12.

Figure 12:
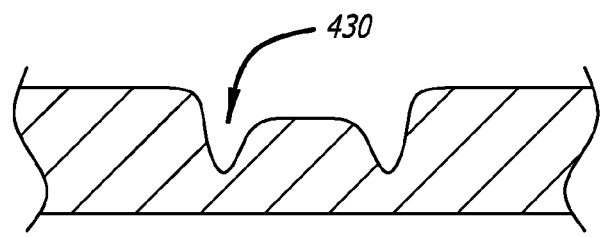
FIG. 12 is a cross sectional view of an ablation profile in a surface that was created using a laser beam having the beam intensity profile of FIG. 11.

As shown in FIG. 12, a beam having an energy profile as shown in FIG. 11 results in a greater depth of cut at the edges of the cut profile than towards the center of cut. Such an intensity profile may be advantageous in that fewer laser pulses may be required to cut entirely through the stent tubing. Cutting the tubing in this matter effectively results in ablating only a ring of material through the full thickness of the work piece, leaving a "plug" as a remnant that is then easily removed during post process. One skilled in the art will understand that focusing the intensity in such a manner will result in faster cutting of the tube than if the beam intensity is shaped in such a manner that the intensity is evenly distributed across the entire area of the beam.

Additionally, a shaped laser beam having an intensity profile as shown in FIG. 11 may be used to form a cut profile such as that shown in FIG. 12. In this manner, craters, divots or indentations 430 may be created in the surface of the tubing. Such divots or indentation can be used to alter the absorption and reflectance characteristics of the surface of the final stent or work piece.

A shaped beam may also be used to mark the stent surface for marketing or functional purposes, such as by producing a barcode, a serial number, or a logo directly on the stent. Such marking could also be used for data tracking. Since the shaped laser beam intensity is well distributed, minimal material would need to be removed to effectively mark the stent, resulting in little, if any, change in the mechanical characteristics of the stent.

Divots or other features formed in the surface of a stent or other device using a shaped laser beam may also be used as reservoirs for the retention of drugs on stent surface. As shown in FIG. 12, a divot or indentation 430 may be formed in the surface of the stent by use of a shaped laser beam having an intensity profile as illustrated in FIG. 11. Such a divot or indentation will have a circumferential dip along the outer edge of the divot or indentation, forming a well into which a drug or polymer may be introduced. Such a profile results in improved retention of a drug or polymer disposed within the well. Further, using a shaped laser beam, the wells can be formed below the surface of the stent, minimizing contact with the surrounding vessel wall during delivery of the stent within a patient's vasculature.

Referring again to FIG. 9, a typical stent cross-section formed using a Gaussian laser beam directed at the central axis of the stent tubing is shown. As can be seen from FIG. 9, the edges of the stent struts are not ideal, rather, they are tapered which is due to the Gaussian energy distribution of the energy of the laser beam. As explained previously, when such a laser beam is used to cut a material, the profile of the cut will be tapered from top to bottom reflecting the Gaussian distribution of intensity of the laser beam. In other words, the diameter of the cut area is greater at the top surface of the material being cut than the diameter of the exit cut located at the bottom of the material being cut.

The tapered profile of a strut edge cut using a Gaussian laser beam is not ideal, since it may result in difficulty in achieving over dimensional stability after the stent strut is electrochemically polished. Moreover, such a profile may not be ideal in terms of the function of the stent strut, which is to oppose a vessel wall when the stent has been implanted inside the lumen of a vessel.

Figure 13:
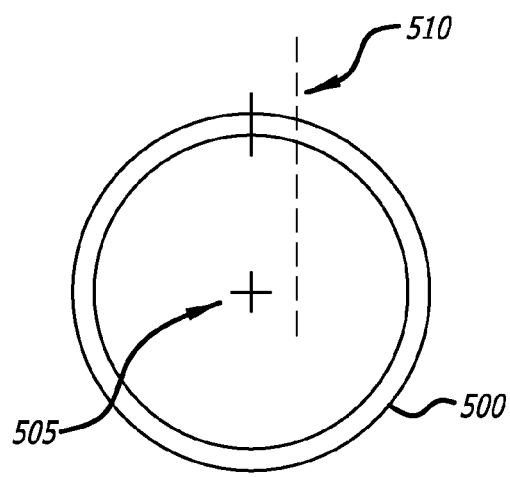
FIG. 13 is a cross-sectional view depicting the central axis of a tubing used into which a stent pattern is to be cut using a laser beam and also showing the beam path of a laser that is directed at the stent tubing along a line that is offset from the tubing central axis.

FIG. 13 shows a cross-section of a length of tubing 500 to be formed into a stent that has been mounted into a collet fixture for laser cutting. Typically, the tubing is positioned under the laser beam such that the laser beam impinges upon the tubing along a radius drawn through the tubing central axis, shown as reference numeral 505. In one embodiment of the present invention, the tubing and laser are instead mounted relative to each other such that the beam path from the laser is no longer directed along a radius of the central axis 505 of the tubing 500, but rather is directed at a path 510 which is offset from the central axis 505 of the tube.

Figure 14:
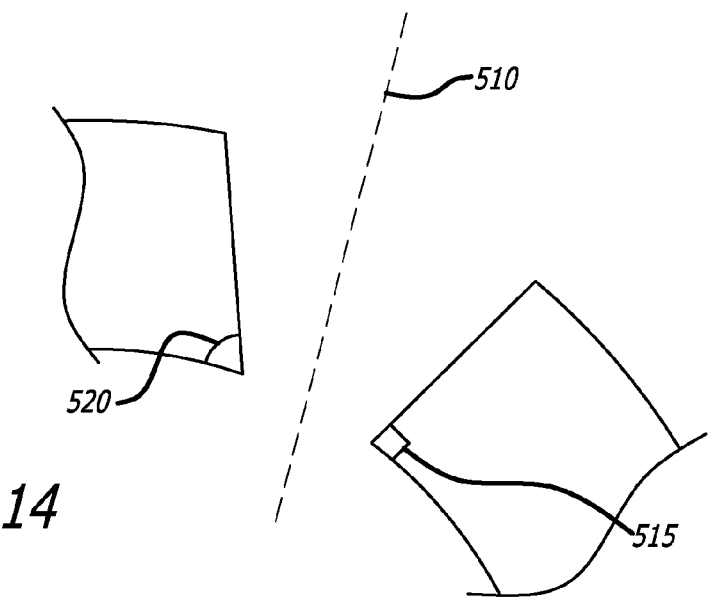
FIG. 14 is a cross-sectional view illustrating a stent strut cut using the offset laser beam of FIG. 13.

FIG. 14 depicts the result of cutting a stent pattern using an off axis beam path 510. As shown, the taper along one edge 515 of the stent strut is steep and approximately perpendicular to the inner strut surface, while the taper along edge 520 of a neighboring strut is not approximately perpendicular, but rather subtends some angle. Because it is desirable to produce a stent strut having two perpendicular sides, a further modification to this system may be made to achieve a completely perpendicular strut cross-section.

Figure 15:
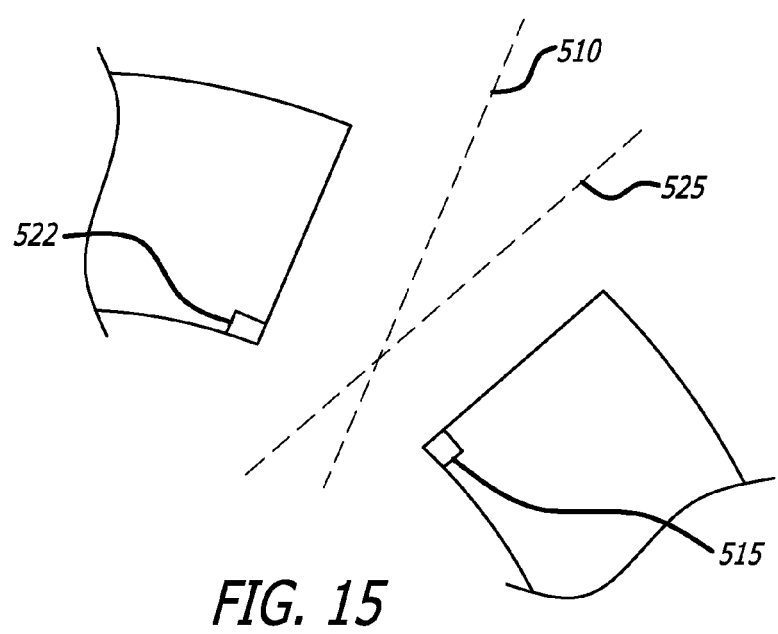
FIG. 15 is a cross-sectional view of stent struts cut using a multiple laser beam system, with one laser beam offset from the central axis of the tubing, and a second laser being offset at a different angle to the central axis of the stent tubing.
Figure 16:
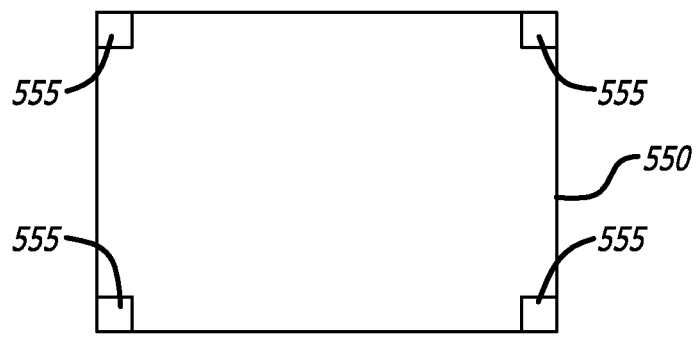
FIG. 16 is a cross-sectional view of an exemplary rectangular stent strut cross-section produced using the multiple offset laser beams shown in FIG. 15.

One embodiment for achieving a completely perpendicular strut cross-section is depicted in FIG. 15. In this embodiment, a second laser is used to direct a laser beam along a separate path 525 which is offset from the central axis of the stent tube and offset from the first path 510. Use of the two laser beams results in cutting two steep sidewalls on adjacent stent struts 515, 522. In this embodiment, the beam spot may be adjusted so that one beam is used to cut one strut wall side and the second beam is used to produce another side of the strut. In this manner, opposing strut walls 515, 522 may be cut such that both strut walls are perpendicular to the bottom and top edges of the respective struts. As depicted in FIG. 16, such a strut 550 will have an approximately rectangular cross-section, as depicted in FIG. 16, with each of the four sides of strut forming an approximate right angle 555 with an adjacent side of the strut. While the strut 550 is illustrated as being square, one skilled in the art will understand that such a strut may also be formed to have a rectangular shape.

Figure 17:
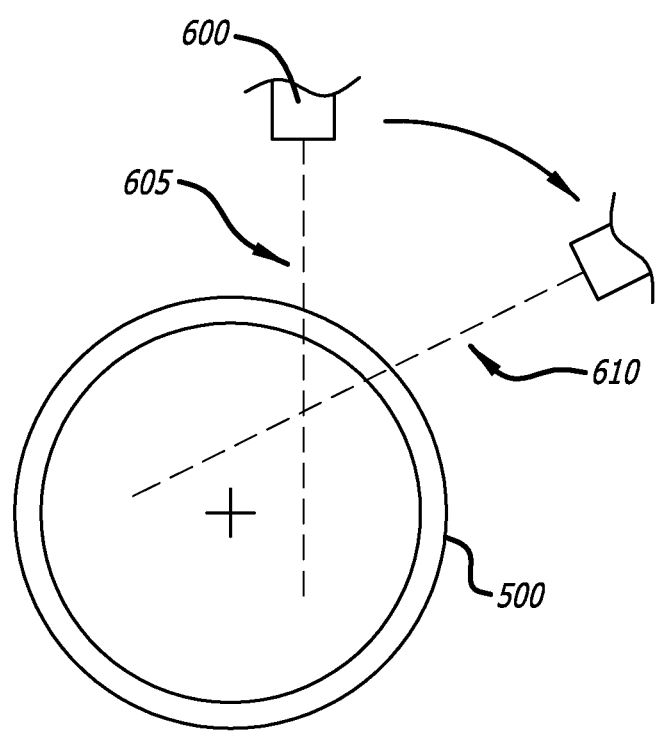
FIG. 17 is a cross-sectional view of another embodiment of the present invention wherein a single laser is used and cuts at a first angle which is offset from the central axis of the tube, and is then moved to a second position at a second angle offset from the central axis of a tube to make a second cut.

FIG. 17 illustrates an alternative embodiment of the present invention wherein a single laser beam may be used to form the strut illustrated in FIG. 16. In this embodiment, a single laser 600 is used to perform a first cut along a path 605 that is offset from the radial axis of tube 500. Laser 600 is then moved relative to the tube such that the beam then impinges the tube 600 along a second path 610. Alternatively, the tube may be shifted relative to the laser beam to achieve the same effect. In still other alternative embodiments, the orientation of the tube 500 and the laser 600 may be moved simultaneously to accomplish the same result.

The process parameters used for pico-second ablation of a stent pattern differ from those used in removing material using conventional thermal process with long laser pulse duration. First, the parameters used to set up the laser are different. Long pulse lasers use a relatively high average power, low peak power and high process gas pressure for stent cutting. Using such settings typically produce stents with undesirable heat-affected zones, rough sidewalls, molten material, and slag.

In contrast, a pico-second or femto-second laser capable of ablating material uses low average power, high peak power and low process gas pressure. Use of such a short pulse laser typically results in a stent having cleaner edges with reduced heat-affected zones, smoother sidewalls and negligible molten material and slag.

Another difference between the use of a thermal process lasers and the ablation process laser is that the motion control program must be set up differently. Unlike lasers which utilize a thermal process to cut the entire stent pattern in a single pass, short pulse lasers that use ablation to cut the stent cut a closed-loop path, commonly referred to as a cell, in the stent pattern using multiple passes before moving onto the next cell. This multiple pass cutting method is necessary because the short pulse laser removes far less material with each pass than a thermal process laser. Accordingly, the pattern cutting times are much longer using a short pulse laser than have typically been experienced using conventional long-pulse thermal processes.

There are many different combinations of movements that can be used to translate a stent beneath a laser beam, or to translate the laser beam over a stent tube. For example, a single-pass method is typically used when the tubing is being cut by a long-pulse thermal affect laser. However, such a single-pass method results in significant heating of the tubing, producing heat affected zones in the stent material as well as production of slag and debris.

The damage caused in the single-pass method may be reduced by use of a multiple-pass method, wherein a significant portion of the stent pattern, or even the entire stent pattern, is cut across the stent using multiple passes of a laser or lasers. Using such a method, the heat input can be reduced for any given pass and consequently the heat-affected zone on the stent is reduced. However, as the laser traverses the tubing in each pass, the ablated material reduces the overall rigidity of the tubing, which may result in a less precise cut of the pattern if the tube flexes or bends during the cutting process.

One embodiment of the present invention utilizes a process referred to hereafter as a cell-multiple-pass method to cut the stent pattern into the stent. In this embodiment, only a single cell of the stent pattern is cut into the tubing at a time. When one cell of the stent is completed, the tubing is traversed to allow the laser to cut the next cell. Using this method and a short pulse laser, each cell may require multiple passes of the laser to cut the pattern. This embodiment is advantageous when compared to the single-pass method because there is less heat input to the tubing for any given pass, thus resulting in a reduction of the heat-affected zone created in the stent. Furthermore, the cell-multiple-pass method is also advantageous over the other multi-pass methods where the entire stent pattern of the stent is cut into the stent using multiple passes of a laser in that the cell-multiple pass method cuts only a single cell at the time, leaving surrounding cells uncut, and thus contributing to the overall rigidity of the tubing, which resulting in a more precise cut during repetitive cutting.

While use of lasers with extremely short pulses, such as a pico-second lasers, have been shown to be effective in generating minimum-slag and sharp and smooth edges and sidewalls, the cutting process does tend to require longer manufacturing times, because less material is removed with each pass of the laser. For example, it may take several times longer for a pico-second laser to cut through stent tubing as it would take a nanosecond or microsecond pulse laser.

Another embodiment of the present invention includes a method for laser cutting of a stent using multiple passes of a laser-cutting beam over the desired stent pattern. In this invention, the first laser pass does not cut through the entire material thickness, but instead forms a groove. For example, the groove may be formed using a nanosecond pulse laser or a microsecond pulse laser such as a fiber laser, and it may have a depth of at least half the material thickness.

After the first pass is completed, one or more additional laser passes are performed using a different laser, such as a short pulse or pico-second laser that completes the cut and forms a better surface finish on the sidewalls. The short pulse laser is passed over the same stent pattern cut by the long pulse laser to cut the material remaining in the base of the groove base to complete cutting pattern through the entire thickness of material being cut. Alternatively, a longer wavelength laser may be used for the first pass or passes followed by use of a shorter wavelength laser to make the final pass. The shorter wavelength laser may be same laser as the longer wavelength laser, with the shorter wavelength light obtained through a frequency conversion of the longer wavelength light.

Figure 18:
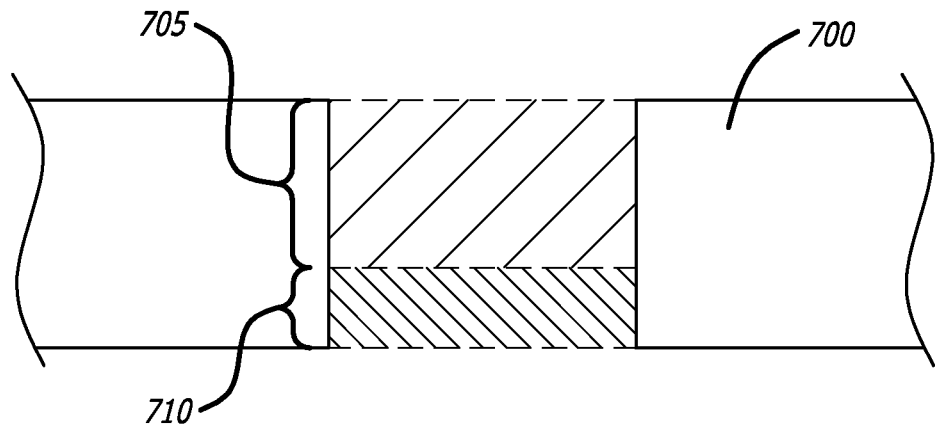
FIG. 18 is a cross-sectional side view of a tubing wall illustrating the depth of cut of a first pass of a laser, and the depth of the cut using a second pass of a laser.

FIG. 18 is a cross-sectional side view of a tubing wall 700 illustrating the results of using such a multi-pass laser cutting system. A first pass region 705 is cut into tube wall 700 using, for example, a nanosecond pulse laser or a microsecond pulse laser. As illustrated in FIG. 18, the first pass region may be at least half of the thickness of the tube wall 700. A second pass region 710, which may include completion of the cut through the entire thickness of tube wall 700, may be cut using a second laser, for example, a short pulse laser, such as a pico-second laser. Use of the short pulse laser results, in a much better wall configuration and finish with a significant reduction in slag formation.

Figure 19:
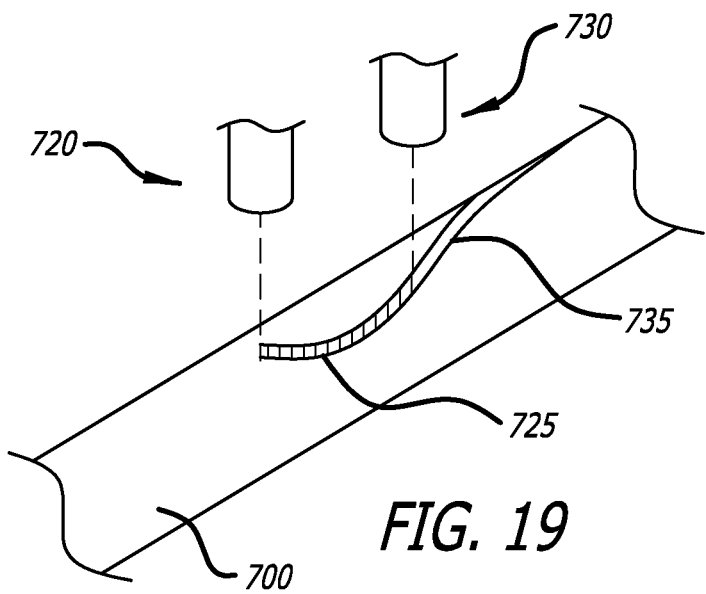
FIG. 19 is a top perspective view depicting use of multiple laser beams to cut a groove and through cut in the surface of a tube.

The consecutive laser passes may occur in series within the same machine, such as is illustrated in FIG. 19. In the embodiment shown FIG. 19, a laser cutting head may include two lasers rather than one. The first pass laser 720 may be, for example, a long pulse, thermal affect laser, such as a conventional Nd:YAG laser, and the second pass laser 730 may be, for example a short pulse, ablation type laser, such as a pico-second laser. A stent tubing 700 mounted in a movement assembly is traversed underneath both the first pass and second pass lasers 720, 730. As the tubing is traversed below the first pass laser 720, a groove 725 is formed. As the tubing continues to be traversed, the groove 725 will eventually fall beneath the second pass laser 720, which will complete the cut 735 of the stent pattern through the thickness of the tube 700. Those skilled in the art will understand that alternatively, the lasers 720 and 730 may be traversed over the tubing and still obtain the same result.

Alternatively, the consecutive laser passes may occur by transferring the stent tube from a first laser cutting station where the first laser pass is made to a second laser cutting station where the second laser pass is made. Such a method requires optics, photodetectors, and computer control necessary to ensure that the second laser pass is performed directly over the groove resulting from the first pass.

In yet another embodiment, a laser that is being capable of being reconfigured from a long pulse laser to a short pulse laser may be used. In this embodiment, the laser may be configured as a long pulse laser and makes the first pass over the stent tubing, cutting a significant portion of the finished depth of the pattern cut. After the first stage of the laser pattern is cut using the laser set in long pulse, thermal, mode, the laser is reconfigured to operate the laser in a short pulse mode to complete an additional pass or passes as necessary to cut the pattern all the way through the stent tubing. Changing the configuration or mode of such a laser requires altering various laser parameters, such as, for example, laser pulse width and power level, which can easily be done under control of a computer processor that is operating under appropriate software command.

One advantage of the various embodiments incorporating or combining a first pass long pulse laser and a second pass short pulse laser is that it balances surface finish and speed of laser cutting. Such a process is capable of creating a stent with an edge quality similar to the edge of the stent shown in FIG. 16 with little if any slag formation. However, since the first laser pass can remove material at a faster rate than the second pass which is performed using the short pulse pico-second laser, the two laser passes can be completed faster than would be possible using a single pass of a short pulse pico-second laser alone.

The various embodiments of the present invention provide for improved control over stent strut geometry, which contributes to greater dimensional stability and may enhance performance characteristics such as wall opposition and stent retention when the stent is implanted in the lumen of a vessel. The various embodiments may also be used to produce other stent geometries, including strut walls that are tapered either toward the inner or outer surface of the stent.

The various embodiments of the present invention are also advantageous in that they may utilize a laser beam that has been shaped using a shaping module to modify the intensity profile of the laser beam. In some embodiments, the shaped laser beam has a more even intensity profile across the relevant beam diameter than is typically delivered by a non-shaped laser beam having a Gaussian profile. Control over such a shaped laser beam produces cleaner surfaces and faster fabrication times. Use of a shaped beam having an alternative energy profile may also result in improved stent characteristics that are advantageous to stent performance and function. For example, shaped laser beam profiles may result in a steeper stent sidewall, which may improve manufacturability and performance of the stent. Moreover, shaped laser beams may result in improved stent cutting speeds, optical characteristics, and drug retention characteristics. It will be understood that the laser beam shaping technology described herein can be used for forming other medical device components, particularly where improved edge surfaces or component fits and the like are required. For example, such a system could be used to produce parts of a guidewire or catheter device. It may also be used to provide for precise machining of pacemaker components.

It will be apparent from the foregoing that the present invention provides a new and improved method and apparatus for direct laser cutting of metal stents enabling greater precision, reliability, structural integrity and overall quality, without burrs, slag or other imperfections which might otherwise hamper stent integrity and performance. Other modifications and improvements may be made without departing from the scope of the invention. Accordingly, it is not intended that the invention be limited, except as by the appended claims.

We claim:

1. A laser cutting system for cutting a stent pattern into a stent, comprising:
   a pico-second laser for producing a laser beam;
   a laser-shaping module capable of altering the intensity profile of the laser beam from a first intensity distribution to a second intensity distribution, the second intensity distribution being a top hat intensity distribution;
   a collimating lens; and
   a focusing lens for focusing the laser beam having the top hat intensity distribution onto a stent tube;
   wherein the laser beam having the top hat intensity distribution is controlled to cut a stent strut having a steep sidewall and improved geometrical uniformity than can be obtained with a laser beam having a Gaussian intensity distribution.

2. The system of claim 1, wherein the laser-shaping module re-maps the first intensity distribution of the laser beam to the second intensity distribution.

3. The system of claim 1, wherein the first intensity distribution is a Gaussian intensity distribution.

* * * * *